US007637659B2

(12) United States Patent
Liu et al.

(10) Patent No.: US 7,637,659 B2
(45) Date of Patent: Dec. 29, 2009

(54) APPARATUS FOR SIMULATION OF HEAT GENERATION OF ELECTRONIC COMPONENTS

(75) Inventors: Tay-Jian Liu, Tu-Cheng (TW); Shang-Chih Liang, Tu-Cheng (TW)

(73) Assignee: Foxconn Technology Co., Ltd., Tu-Cheng, Taipei Hsien (TW)

( * ) Notice: Subject to any disclaimer, the term of this patent is extended or adjusted under 35 U.S.C. 154(b) by 598 days.

(21) Appl. No.: 11/309,183

(22) Filed: Jul. 7, 2006

(65) Prior Publication Data

US 2007/0071063 A1    Mar. 29, 2007

(30) Foreign Application Priority Data

Aug. 19, 2005    (CN) .................... 2005 1 0036768

(51) Int. Cl.
*G01K 1/00*    (2006.01)
*G01K 7/00*    (2006.01)
(52) U.S. Cl. .................... 374/208; 374/179; 374/29; 374/43; 374/152; 324/765

(58) Field of Classification Search .................... 374/5, 374/208, 179, 29, 43, 152, 57; 324/765
See application file for complete search history.

(56) References Cited

U.S. PATENT DOCUMENTS

| 5,969,949 | A  | * | 10/1999 | Kim et al. .................... 361/704 |
| 6,663,278 | B1 | * | 12/2003 | Chien et al. .................... 374/43 |
| 6,744,269 | B1 | * | 6/2004 | Johnson et al. ............. 324/760 |
| 6,886,976 | B2 | * | 5/2005 | Gaasch et al. .................. 374/5 |

* cited by examiner

*Primary Examiner*—Gail Verbitsky
*Assistant Examiner*—Mirellys Jagan
(74) *Attorney, Agent, or Firm*—Frank R. Niranjan

(57) ABSTRACT

Disclosed is an apparatus (10) for simulation of heat generation of a heat-generating electronic component. The apparatus includes a heat-transfer simulation device (110), a base (120) and at least one supporting post (150). The base is made of a heat-insulation material, and defines therein a recess (122). The heat-transfer simulation device is used for simulating heat generation from a heat-generating electronic component. The supporting post supportively mounts the heat-transfer simulation device within the recess defined in the base. A method of evaluating heat removal capacity of a heat dissipation device is also disclosed based on this apparatus.

6 Claims, 6 Drawing Sheets

APPARATUS FOR SIMULATION OF HEAT GENERATION OF ELECTRONIC COMPONENTS

FIELD OF THE INVENTION

The present invention relates to apparatuses for evaluation of heat removal capacity of heat dissipation devices, and more particularly to an apparatus for simulation of heat generation of a particular heat-generating electronic component with reduced overall heat loss so that the evaluation process can be carried out with improved accuracy.

DESCRIPTION OF RELATED ART

It is well known that heat is produced by heat-generating electronic components during their normal operations. For example, a central processing unit (CPU) mounted within a computer enclosure generates a large amount of heat. The generated heat, if not adequately removed from the enclosure, will noticeably degrade the performance of the CPU. Thus, a heat dissipation device is required for cooling of the CPU.

When a heat dissipation device is used to remove excessive heat from a particular heat-generating electronic component (e.g. a CPU), the heat dissipation device should be evaluated beforehand to ensure that it has an adequate heat removal capacity for taking away the heat generated by the CPU effectively and efficiently, especially when the heat dissipation device is a new design. In practice, the evaluation process is often carried out using a heat-transfer simulation device to simulate the heat generation of a CPU. To reduce heat loss, the heat-transfer simulation device generally is disposed on a supporting base, with only a heat-emitting surface of the heat-transfer device being exposed for thermally contacting the heat dissipation device to be evaluated. A heating device is then employed to input thermal energy to the heat-transfer simulation device, which in turn, transfers the thermal energy to the heat dissipation device through the heat-emitting surface.

In this evaluation process, the thermal energy inputted by the heating device is deemed as being absorbed and dissipated entirely by the heat dissipation device. The maximum amount of thermal energy that the heat dissipation device can dissipate is accordingly used to evaluate the heat removal capacity of the heat dissipation device. However, since the heat-transfer simulation device is directly seated in and contacts with the supporting base, a portion of the thermal energy inputted by the heating device will also be absorbed and dissipated by the supporting base, even if the supporting base is made of a heat-insulation material. As such, the heat actually dissipated by the heat dissipation device is much less than the thermal energy as being originally inputted by the heating device. The heat removal capacity of the heat dissipation device, if directly based on the thermal energy inputted by the heating device without considering the heat loss associated with the supporting base, will result in overly optimistic evaluation results. For example, if the thermal energy inputted by the heating device is 80 watts while the heat loss associated with the supporting base is 10 watts, then the heat actually absorbed and dissipated by the heat dissipation device will be 70 watts. Thus, an error of 10 watts will exist in the above-mentioned evaluation process.

In view of the above-mentioned disadvantage, it is desirable to provide an apparatus which can be applied to evaluate the heat removal capacity of the heat dissipation device with improved measurement accuracy.

SUMMARY OF THE INVENTION

The present invention in one aspect relates to an apparatus for simulation of heat generation of a heat-generating electronic component. The apparatus includes a base, a heat-transfer simulation device and at least one supporting post. The base is made of a heat-insulation material, and defines a recess therein. The heat-transfer simulation device is used for simulating heat generation of the heat-generating electronic component. The supporting post supportively mounts the heat-transfer simulation device within the recess defined in the base. The heat-transfer simulation device does not have a physical contact with the base.

The present invention in another aspect, relates to a method of evaluating heat removal capacity of a heat dissipation device. The method includes the following steps: (1) providing a base made of a heat-insulation material, wherein the supporting base defines therein a recess; (2) providing a heat-transfer simulation device for simulation of heat generation of a heat-generating electronic component; (3) providing at least one supporting post for supportively mounting the heat-transfer simulation device within the recess defined in the base, wherein the heat-transfer simulation device does not have a physical contact with the base; (4) maintaining the heat dissipation device in thermal contact with the heat-transfer simulation device; (5) inputting thermal energy to the heat-transfer simulation device; and (6) measuring temperature of the heat-transfer simulation device to obtain the heat removal capacity of the heat dissipation device according to the measured temperature and the inputted thermal energy.

Other advantages and novel features of the present invention will become more apparent from the following detailed description of preferred embodiments when taken in conjunction with the accompanying drawings, in which:

DETAILED DESCRIPTION OF THE INVENTION

Figure 1:
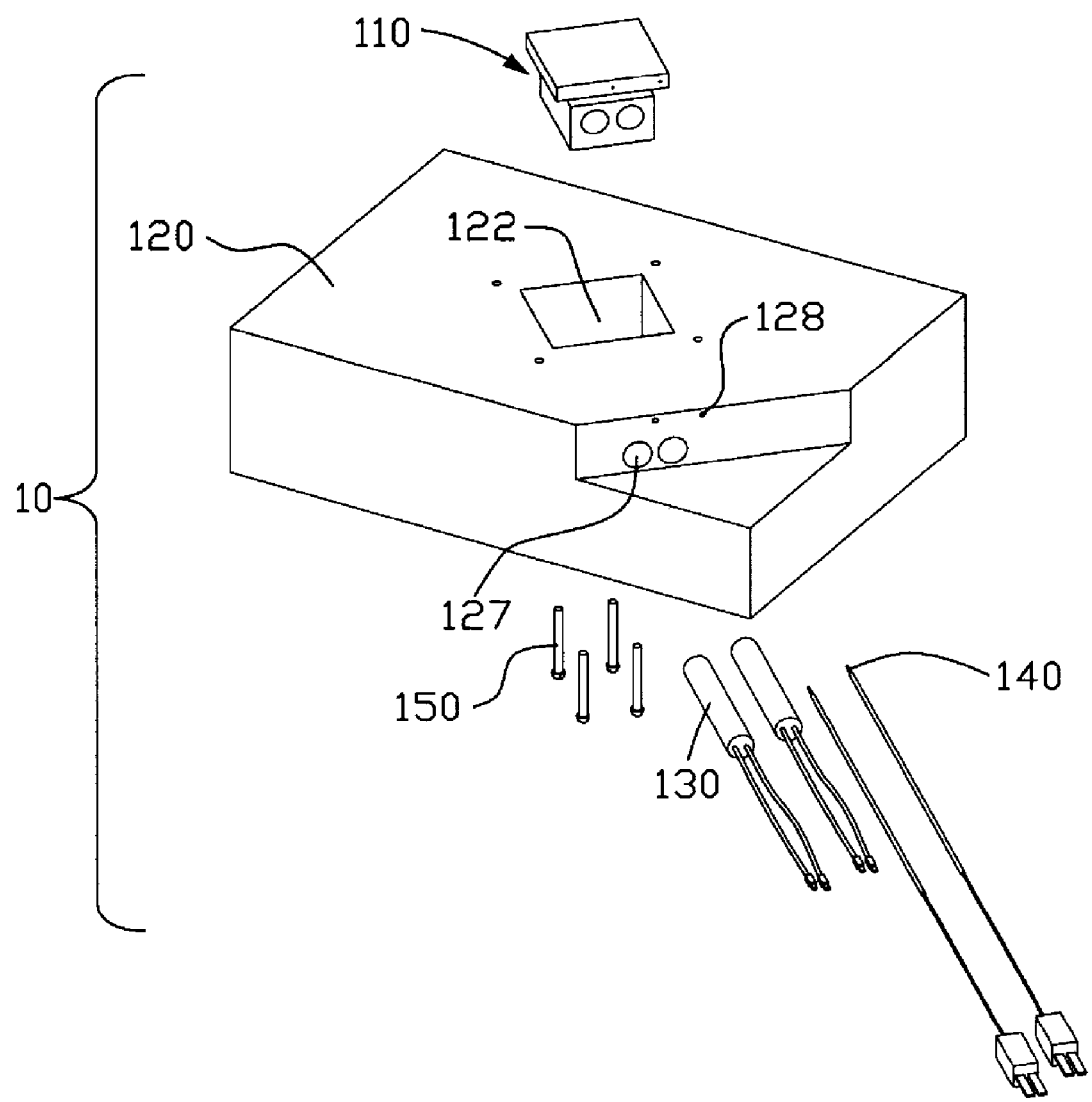
FIG. 1 is an exploded, isometric view of an apparatus for simulation of heat generation of a particular heat-generating component in accordance with an embodiment of the present invention.

FIG. 1 illustrates an apparatus 10 for simulation of heat generation of a heat source in accordance with an embodiment of the present invention. The apparatus 10 can be suitably used to evaluate the heat removal capacity of a particular heat dissipation device (not shown). The apparatus 10 in this embodiment is especially suitable for simulating heat generation of a heat-generating electronic device such as a central processing unit (CPU) of a computer. An evaluation process can be carried out on the apparatus 10 to evaluate whether this particular heat dissipation device has an adequate heat removal capacity for cooling the CPU.

The apparatus 10 includes a heat-transfer simulation device 1110, a supporting base 120, a pair of electrical heaters 130, a pair of thermocouples 140, and four supporting posts 150. The supporting base 120 is made of a heat-insulation material, such as plastics, rubbers, acrylonitrile butadiene styrene (ABS), bakelite, or the like. The supporting base 120 defines a rectangular (or square) recess 122 at a central portion thereof for reception of the heat-transfer simulation device 110 therein. A pair of first guiding holes 127 is defined from a corner of the supporting base 120 to communicate with the recess 122, thus allowing insertion of the electrical heaters 130. A pair of second guiding holes 128 is also defined from the corner to communicate with the recess 122, allowing the insertion of the thermocouples 140. The first guiding holes 127 are located below the second guiding holes 128. Each of the supporting posts 150 has a large length-to-diameter ratio. In this embodiment, the supporting posts 150 are in the form of a plurality of screws.

Figure 2:
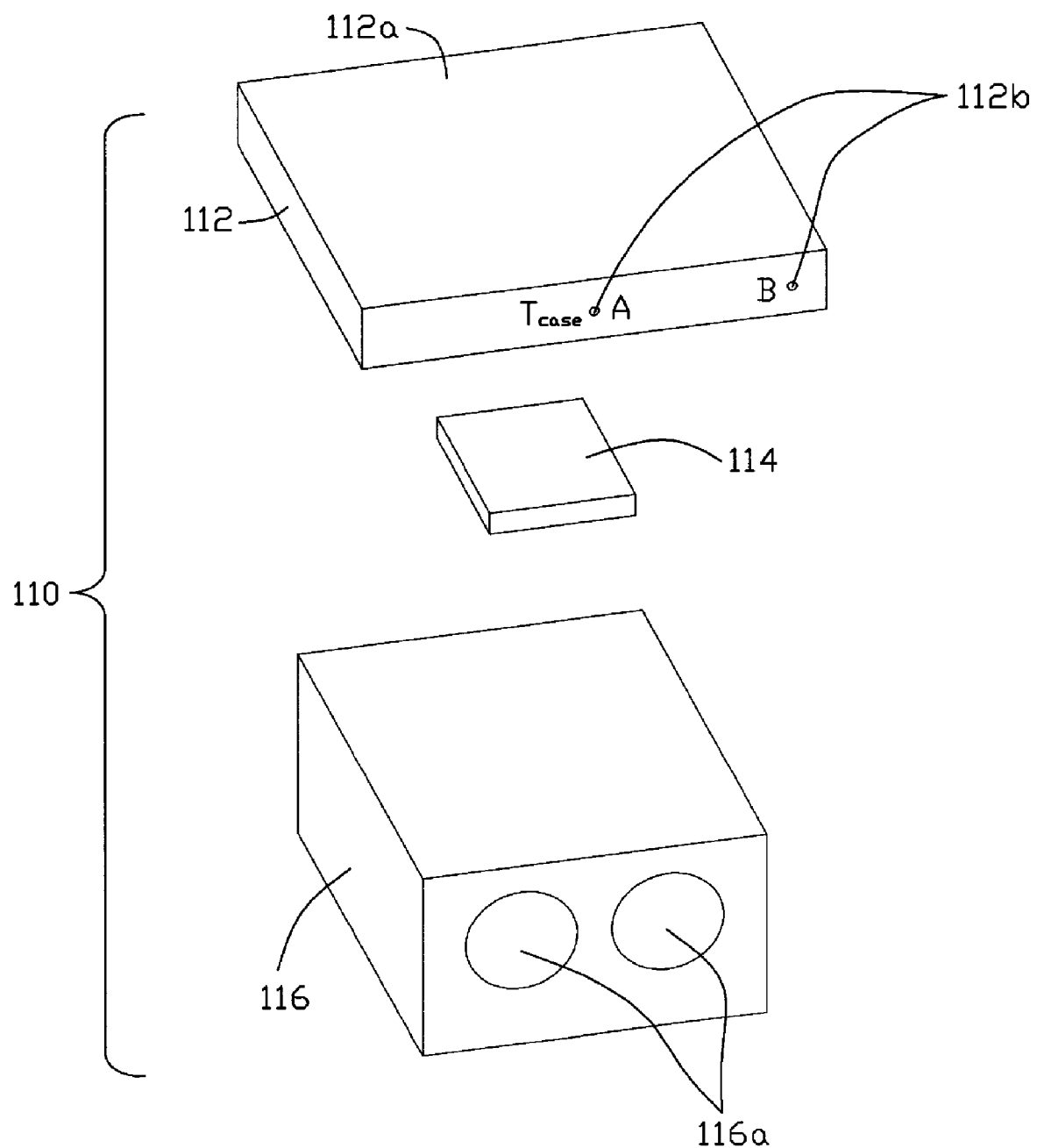
FIG. 2 is an exploded, isometric view of a heat-transfer simulation device according to the embodiment of FIG. 1.

With reference to FIG. 2, the heat-transfer simulation device 110 includes a contacting plate 112, a core element 114 and a heat-receiving block 116. The contacting plate 112 has an upper surface 112a. In the contacting plate 112, temperature detecting points A and B are established, wherein the temperature detecting point A is located near a central portion of the contacting plate 112 while the temperature detecting point B is located near a lateral side of the contacting plate 112. "Temperature detecting point" used herein means a physical location that represents a point for which temperature control is desired. In order to detect the temperatures at the temperature detecting points A and B, a pair of retention holes 112b are correspondingly defined from a front side of the contacting plate 112 wherein each retention hole 112b receives and positions one of the thermocouples 140 therein.

The core element 114 is located between the contacting plate 112 and the heat-receiving block 116. The core element 114 has a much smaller size than the contacting plate 112 so as to simulate the heat generation of a CPU in a more accurate manner. The heat-receiving block 116 defines a pair of mounting holes 116a from a front side thereof wherein each mounting hole 116a receives and positions one of the electrical heaters 130 therein.

Figure 3:
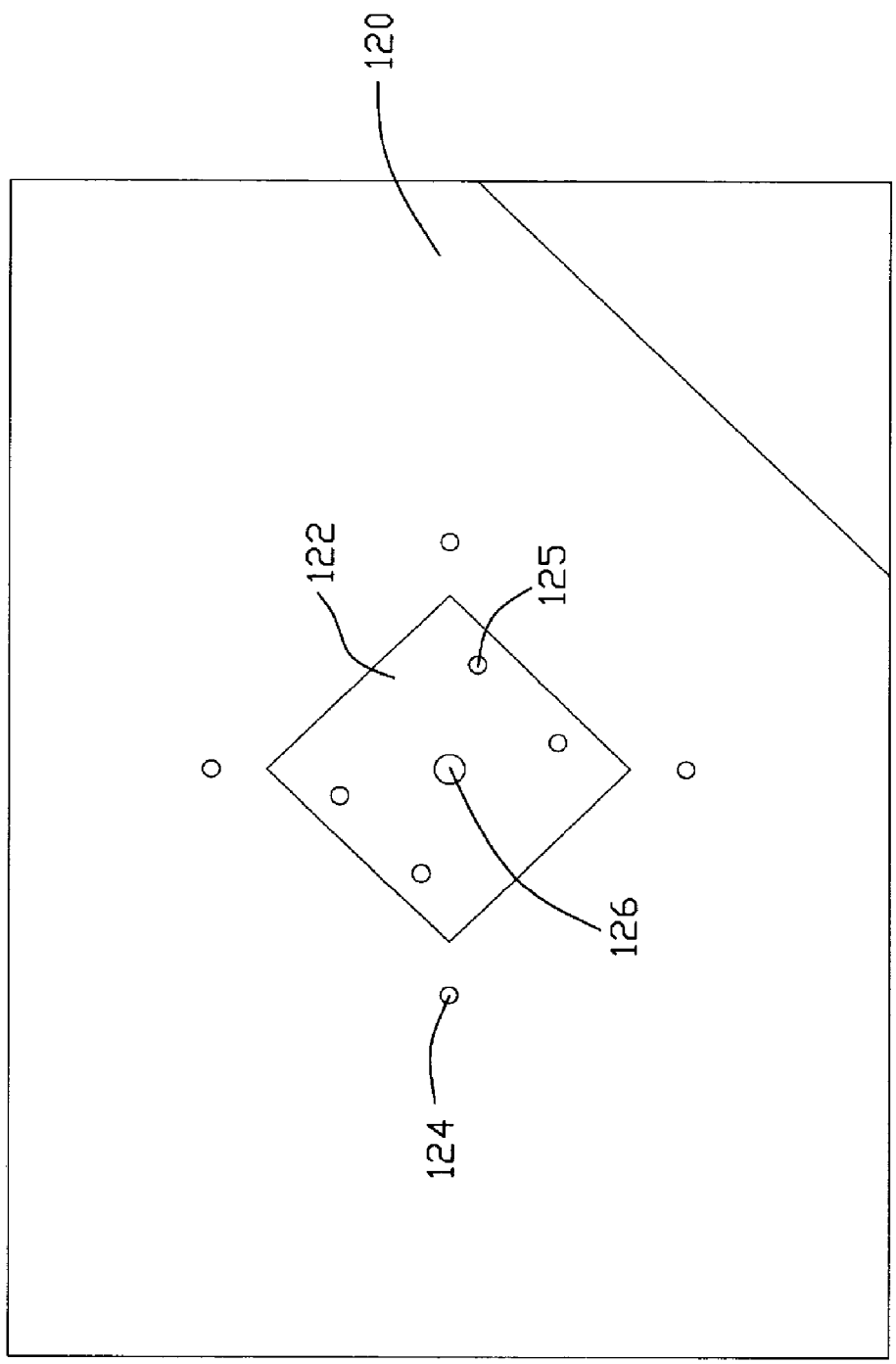
FIG. 3 is a top plan view of a supporting base according to the embodiment of FIG. 1.
Figure 5:
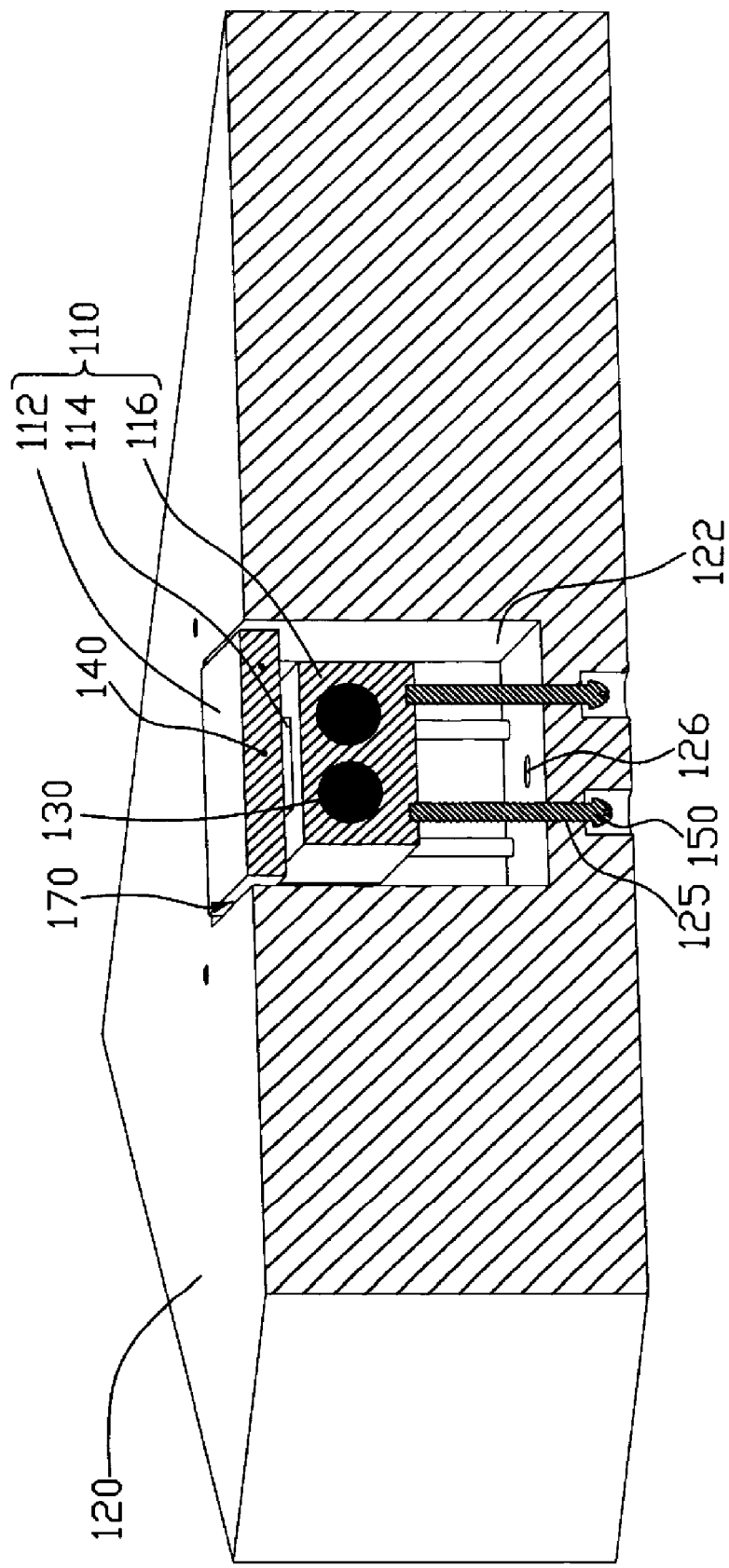
FIG. 5 is a cross-sectional view of the apparatus of FIG. 4.

Referring now to FIG. 3, the supporting base 120 defines at a top surface thereof four mounting holes 124. The mounting holes 124, which cooperatively surround the recess 122 defined in the supporting base 120, are used to mount the heat dissipation device to be evaluated. Additionally, four threaded holes 125 and a central hole 126 are defined from a bottom surface of the supporting base 120 to communicate with the recess 122, as also shown in FIG. 5. The central hole 126 is surrounded by the four threaded holes 125. The central hole 126 is designed to allow a detaching tool, for example, a pin (not shown) to insert into from the bottom surface of the supporting base 120 and facilitate detachment of the heat-transfer simulation device 110 from the recess 122 of the supporting base 120.

Figure 4:
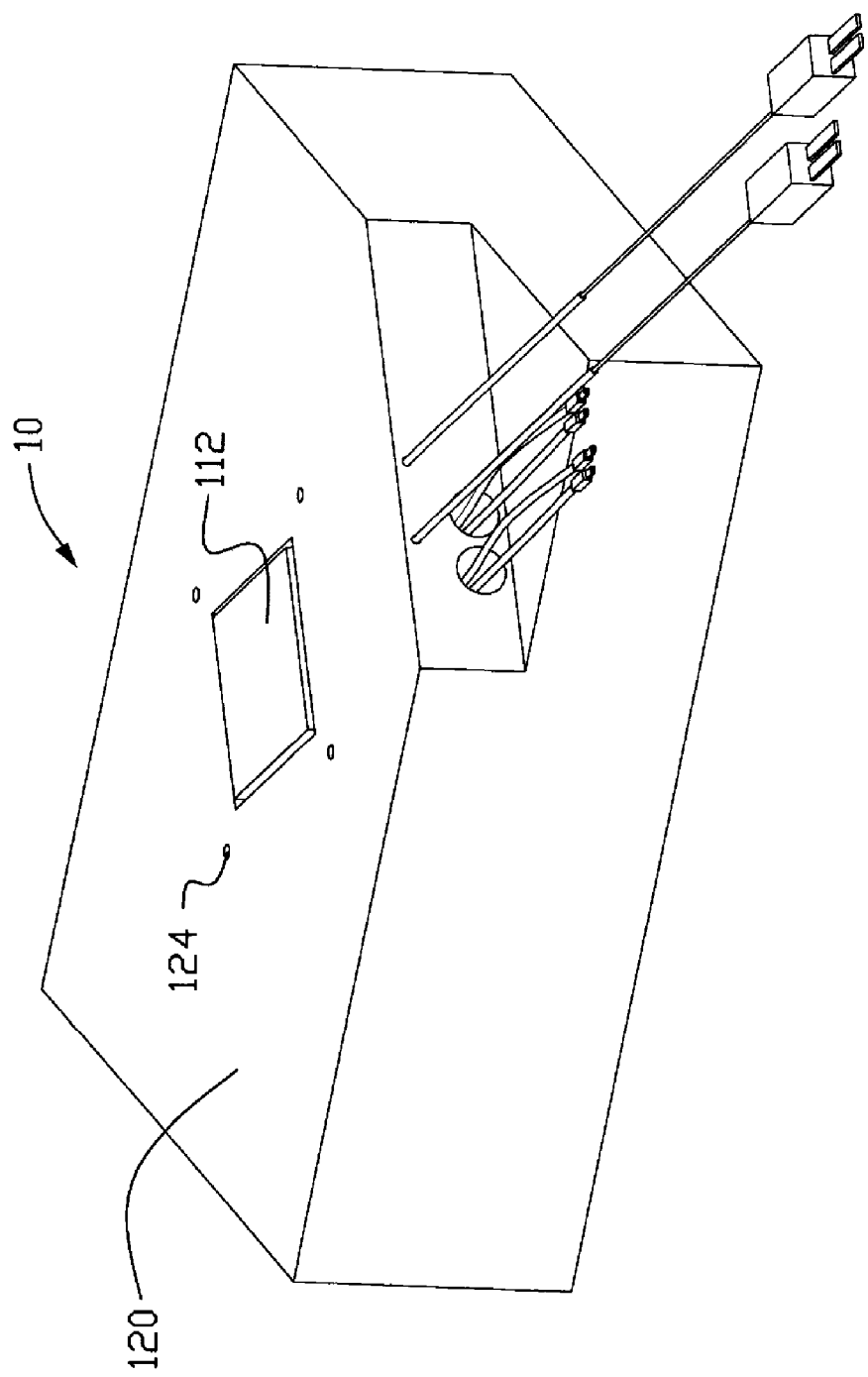
FIG. 4 is an assembled view of the apparatus of FIG. 1.

With reference to FIGS. 4-5, in assembly, the heat-transfer simulation device 110 is mounted within the recess 122 of the supporting base 120 by the four supporting posts 150 engaging with the supporting base 120 in the four threaded holes 125. The upper surface 112a of the contacting plate 112 protrudes slightly above the top surface of the supporting base 120 so that the heat dissipation device to be evaluated can be maintained in intimate thermal contact with the contacting plate 112. A gap 170 is formed between an inner circumferential surface of the recess 122 and an outer circumferential surface of the heat-transfer simulation device 110, whereby the heat-transfer simulation device 110 is not brought into direct contact with the supporting base 120.

The electrical heaters 130 are guided through the first guiding holes 127 of the supporting base 120 and are ultimately inserted into and positioned in the mounting holes 116a defined in the heat-receiving block 116. The electrical heaters 130 and the heat-receiving block 116 preferably have a layer of thermal interface material therebetween so as to increase heat transfer efficiency. The thermocouples 140 are guided by the second guiding holes 128 of the supporting base 120 and then inserted into and positioned in the retention holes 112b defined in the contacting plate 112.

Then, the heat dissipation device to be evaluated is thermally connected to the upper surface 112a of the contacting plate 112. Thermal energy is inputted to the heat-receiving block 116 by the electrical heaters 130. The thermal energy then is transferred to the core element 114 from the heat-receiving block 116. The core element 114 absorbs the thermal energy from the heat-receiving block 116 and then spreads the thermal energy to the above contacting plate 112. The contacting plate 112 then transfers the thermal energy, via the upper surface 112a, to the heat dissipation device where the thermal energy is finally dissipated into ambient air. In this embodiment, the core element 114 and the contacting plate 112 cooperatively simulate heat generation of a CPU.

During the evaluation process, the thermocouples 140 are used to detect the temperatures at the temperature detecting points A and B when the thermal equilibrium is established between the heat dissipation device and the heat-transfer simulation device 110. The heat dissipation device can be evaluated based on the temperature at the temperature detecting point A, or the temperatures at the temperature detecting points A and B. For example, if the heat dissipation device is evaluated based merely on the temperature at the temperature detecting point A, the temperature Tcase at the temperature detecting point A is first obtained by one of the thermocouples 140. If the detected temperature Tcase at the temperature detecting point A is lower than a predetermined level, for example, 50° C., then the electrical heaters 130 gradually increase the amount of thermal energy inputted to the heat-transfer simulation device 110, until the temperature Tcase at the temperature detecting point A reaches the predetermined level (i.e. 50° C.). At this moment, the thermal energy inputted by the electrical heaters 130 is used to evaluate the heat removal capacity of the heat dissipation device.

Figure 6:
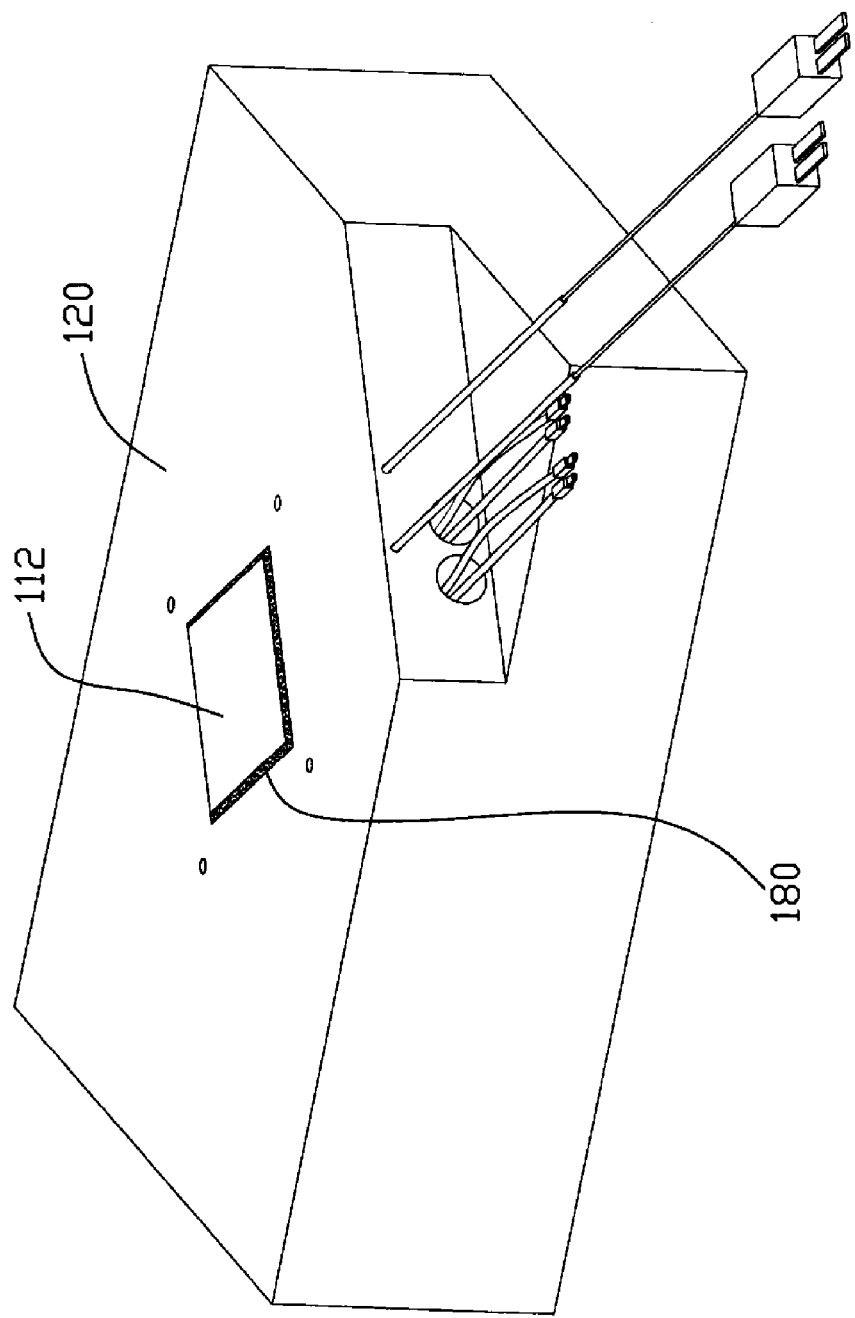
FIG. 6 is similar to FIG. 4, with a gap between the supporting base and the heat-transfer simulation device being filled with a soft material.

In the evaluation process, the heat-transfer simulation device 110, as supported by the supporting posts 150, is "suspended" (i.e. held) in the recess 122 of the supporting base 120 and is not brought into direct contact with the supporting base 120; thus, the thermal energy inputted to the heat-transfer simulation device 110 is effectively prevented from being conducted or transferred to the supporting base 120 and hence the heat loss associated with the supporting base 120 in the whole evaluation process is greatly reduced, thereby increasing the measurement accuracy for the heat dissipation device. The gap 170 formed between the supporting base 120 and the heat-transfer simulation device 110 may optionally be filled with soft, heat-insulation material such as a layer of cotton wadding 180, as shown in FIG. 6, so as to steadily position the heat-transfer simulation device 110 in the recess 122.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An apparatus for simulation of heat generation of a heat-generating electronic component, comprising:
    a base made of a heat-insulation material, the base defining a recess therein;
    a heat-transfer simulation device adapted for simulating heat generation of said heat-generating electronic component; and
    at least one supporting post supportively mounting the heat-transfer simulation device within said recess;
    wherein the heat-transfer simulation device includes a contacting plate adapted for thermally contacting a heat dissipation device, a heat-receiving block adapted for receiving thermal energy from a heating device, and a core element sandwiched between the contacting plate and the heat-receiving block; and
    wherein the contacting plate defines a hole at a lateral side thereof for receiving of a thermocouple therein.

2. The apparatus of claim 1, wherein the contacting plate has a larger size than the core element.

3. The apparatus of claim 1, wherein the heat-receiving block defines a hole at a lateral side thereof for receiving of an electrical heater therein.

4. The apparatus of claim 1, wherein the at least one supporting post is in the form of screw.

5. The apparatus of claim 1, wherein a gap is formed between an outer surface of the heat-transfer simulation device and an inner surface of the recess.

6. The apparatus of claim 5, wherein the gap is filled up with a soft, heat-insulation material.

* * * * *

UNITED STATES PATENT AND TRADEMARK OFFICE
CERTIFICATE OF CORRECTION

PATENT NO.      : 7,637,659 B2  Page 1 of 1
APPLICATION NO. : 11/309183
DATED           : December 29, 2009
INVENTOR(S)     : Liu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 773 days.

Signed and Sealed this

Ninth Day of November, 2010

David J. Kappos
*Director of the United States Patent and Trademark Office*